United States Patent [19]

Voege et al.

[11] Patent Number: 4,749,577

[45] Date of Patent: Jun. 7, 1988

[54] PROCESS FOR THE PRODUCTION OF DUST-FREE OLAQUINDOX-CONTAINING FEEDSTUFF MIXES

[75] Inventors: Herbert Voege; Hans-Ulrich Sieveking, both of Leverkusen, Fed. Rep. of Germany

[73] Assignee: Bayer Aktiengesellschaft, Leverkusen, Fed. Rep. of Germany

[21] Appl. No.: 875,165

[22] Filed: Jun. 17, 1986

[30] Foreign Application Priority Data

Jun. 27, 1985 [DE] Fed. Rep. of Germany ....... 3522937

[51] Int. Cl.$^4$ .............................................. A23K 1/00
[52] U.S. Cl. ........................................ 426/74; 426/97; 426/99; 426/335; 426/532; 426/807
[58] Field of Search ................ 426/74, 623, 630, 543, 426/97, 99, 807, 532, 335; 424/250

[56] References Cited

U.S. PATENT DOCUMENTS 3,468,667  9/1969  Chandler et al. ..................... 426/97
4,211,781  7/1980  Chapman ............................. 426/630

FOREIGN PATENT DOCUMENTS 0134444  3/1985  European Pat. Off. .
2541459  4/1976  Fed. Rep. of Germany .

OTHER PUBLICATIONS

Bayer Derwent Publication C85-008101, Jan. 17, 1985.

*Primary Examiner*—R. B. Penland
*Attorney, Agent, or Firm*—Sprung Horn Kramer & Woods

[57] ABSTRACT

A process for the production of an olaquindox-containing non-dusting livestock feedstuff mix, comprising
(a) mixing 75 to 98.5% by weight of an inorganic carrier material acceptable for livestock nutrition and having a maximum of the particle size distribution between 0.1 and 1.0 mm
(b) with 0.5-5% by weight of a non-toxic oil and/or an emulsifier acceptable for livestock nutrition, and
(c) to the mixture adding 1-20% by weight of olaquindox.

3 Claims, No Drawings

PROCESS FOR THE PRODUCTION OF DUST-FREE OLAQUINDOX-CONTAINING FEEDSTUFF MIXES

The present invention relates to a process for the production of dust-free olaquindox-containing feedstuff mixes and to feedstuff mixes which are produced by this process.

Olaquindox (2-[N-(2-hydroxyethyl)carbamoyl]-3-methylquinoxaline 1,4-dioxide) is used as active compound in livestock feedstuff mixes. Difficulties have arisen with the production of dust-free olaquindox-containing livestock feedstuff mixes.

It is known to reduce the formation of dust during the production of a mix containing active compound by application of an active compound solution or suspension to carrier materials and to immobilize it on the carrier, where appropriate with the addition of polymers.

It is likewise known initially to mix organic carrier materials with oil, to add active compounds such as, for example, quinoxaline 1,4-dioxides, and to admix further oil to this mixture (DE-OS (German Published Specification) No. 2,541,459).

The present invention relates to a process for the production of olquindox-containing dust-free livestock feedstuff mixes, which is characterized in that (a) 75 to 98.5% by weight of an inorganic carrier material which is approved for livestock nutrition and has a maximum of the particle size distribution between 0.1 and 1.0 mm is mixed with (b) 0.5-5% by weight of a non-toxic oil and/or with an emulsifier approved for livestock nutrition, and to this mixture is added (c) 1-20% by weight of olaquindox and, where appropriate, other auxiliaries.

Organic carrier materials as are used according to the state of the art for the production of dust-free feedstuff mixes have the disadvantage that they are relatively costly. In addition, they give rise to problems during storage in that they must be protected from attack by pests. Furthermore, effort is involved in producing them in a uniform particle size distribution.

All these disadvantages can be avoided by the use of inorganic carrier materials. However, the application of the active compound olaquindox onto the inorganic carrier materials using the substances approved as feedstuff additives gives rise to difficulties. Oils only poorly wet the inorganic carrier. They form small droplets on its surface. This leads to non-uniform application of the active compound and to aggregation of the mix once the mixing process is complete.

These difficulties can be overcome by the use of a mixture of oil and emulsifier or by operating with emulsifier alone.

Suitable carrier materials are all inorganic materials which can be used in livestock nutrition. Those which are preferred are, but not exclusively, limestone (calcium carbonate), sodium chloride or calcium phosphates. The particle size of these carriers should not be below or above a particular value. When powders are used the particles clump together. If the particle size of the material is too large, the distribution of the active compound in the final feed is inhomogeneous, and demixing may occur. The carriers must thus have a maximum in the particle size distribution between 0.1 and 1 mm.

Suitable oils are all oils of vegetable origin, thus, for example, sunflower oil, maize germ oil, sesame oil, and cottonseed oil. However, liquid paraffins can also be used.

Suitable emulsifiers are all those which can be used in feedstuffs.

These are, for example, higher alkyl esters of acetic acid, lactic acid, tartaric acid, citric acid, monoacetyltartaric and diacetyltartaric acid, monoglycerides and diglycerides of edible fatty acids, esters of sugars, such as, for example, sucrose, with edible fatty acids, glycerol polyethylene glycol ricinoleate, monoesters of edible fatty acids with 1, 2 propylene glycol or polyethylene glycols.

Examples of other auxiliaries are antioxidants such as butylhydroxytoluene, ascorbyl palmitate, tocopherol or ethoxyquine, also aromatics and flavorings or colorants.

In olaquindox feedstuff mixes and premixes, preferably between 1% and 20%, preferably between 2% and 15%, of the active compound is used. Accordingly, the proportion of the carrier is between 75% and 98.5%, preferably between 80% and 97.5%.

Suitable carriers which are preferred are calcium carbonate, sodium chloride and sec. calcium phosphate.

The maximum of the particle size distribution of the carrier which is used is between 0.1 mm and 1.0 mm, preferably between 0.1 mm and 0.8 mm.

The proportion of the oil and/or emulsifier can vary, depending on the nature of the carrier, between 0.5 and 5% by weight, preferably between 1 and 3% by weight.

Suitable oils are preferably oils of vegetable origin, such as groundnut oil, sunflower oil or soy oil. Monoglycerides and diglycerides of edible fatty acids, glycerol polyethylene glycol ricinoleate, propylene glycol monoesters, polyethylene glycol esters of edible fatty acids and sugar esters are preferably found suitable as emulsifiers.

To produce the claimed formulations, the carrier is initially introduced into a conventional mixer. The oil solution and/or emulsifier solution is added to the mixer while it is running—possibly with other auxiliaries—and mixing is continued until the carrier material is uniformly wetted. The mixing time depends on the nature of the mixer. The active compound is then added, and mixing is continued until a homogeneous mix has been produced.

The examples which follow are intended to illustrate the claimed formulations but not to restrict them.

The production of the premixes is carried out in the manner detailed above. The figures after the carrier indicate the maximum of the particle distribution.

EXAMPLE 1

| | |
|---|---|
| Sodium chloride 0.2 mm | 88.0 g |
| Mono/diglyceride mixture of fatty acids | 2.0 g |
| Olaquindox | 10.0 g |
| | 100.0 g |

EXAMPLE 2

| | |
|---|---|
| Calcium carbonate | 97.0 g |
| Groundnut oil plus 0.1% antioxidant | 0.5 g |
| Glycerol polyethylene glycol ricinoleate | 0.5 g |
| Olaquindox | 2.0 g |

-continued

| | |
|---|---|
| | 100.0 g |

The oil and emulsifier are mixed before use.

EXAMPLE 3

| | |
|---|---|
| sec. Calcium phosphate 0.4 mm | 85.0 g |
| Glycerol polyethylene glycol ricinoleate | 5.0 g |
| Olaquindox | 10.0 g |
| | 100.0 g |

EXAMPLE 4

| | |
|---|---|
| Calcium carbonate 0.2 mm | 85.0 g |
| Sunflower oil + 0.1% antioxidant | 1.5 g |
| Monoglyceride fatty acid esters | 0.5 g |
| Olaquindox | 5.0 g |
| | 100.0 g |

The oil and emulsifier are mixed before use.

EXAMPLE 5

| | |
|---|---|
| Calcium carbonate 0.2 mm | 88.5 g |
| Glycerol polyethylene glycol ricinoleate | 1.5 g |
| Olaquindox | 10.0 g |
| | 100.0 g |

The formulations according to the above examples were subjected to a dusting test comparing with conventional olaquindox feedstuff mixes. This entails dust being generated in a commercially available test apparatus. Air is sucked through the apparatus under defined conditions, and the dust is trapped on a membrane filter. The filter is tested for deposition of active compound by a HPLC analytical method. For details of the test, see D. Stauber and R. Beutel, Fresenins Z. Anal. Chem. (1984) 318, 522-524.

Whereas olaquindox dust could be detected with the conventional olaquindox feedstuff mixes, this was not the case with formulations according to the above examples.

It is understood that the specification and examples are illustrative but not limitative of the present invention and that other embodiments within the spirit and scope of the invention will suggest themselves to those skilled in the art.

We claim:

1. A process for the production of an olaquindox-containing non-dusting livestock feedstuff mix, comprising
    (a) mixing 75 to 98.5% by weight of an inorganic carrier material acceptable for livestock nutrition, having a maximum of the particle size distribution between 0.1 and 1.0 mm and consisting essentially of a carrier material selected from the group consisting of calcium carbonate and sodium chloride,
    (b) with 0.5-5% by weight of a non-toxic oil and/or an emulsifier acceptable for livestock nutrition, and
    (c) to the mixture adding 1-20% by weight of olaquindox.

2. The process according to claim 1, wherein in (b) there is employed a higher alkyl ester of lactic acid, acetic acid, tartaric acid or citric acid, a monoglyceride or diglyceride of an edible fatty acid, glycerol polyethylene glycol ricinoleate, a 1,2-propylene glycol monoester or polyethylene glycol ester of an edible fatty acid, or an ester of a sugar and an edible fatty acid.

3. A non-dusting olaquindox-containing feedstuff mix comprising by weight
    (a) 75 to 98.5% of an inorganic carrier material acceptable for livestock nutrition and having a maximum of the particle size distribution between 0.1 and 1.0 mm and consisting essentially of a carrier material selected from the group consisting of calcium carbonate and sodium chloride,
    (b) 0.5 to 5% of a non-toxic oil and/or an emulsifier acceptable for livestock nutrition, and
    (c) 1 to 20% of olaquindox,
    (a) plus (b) plus (c) totalling 100%.

* * * * *